United States Patent [19]

Honkawa et al.

[11] 4,429,230
[45] Jan. 31, 1984

[54] FLUORESCENCE POLARIZATION ANALYZER

[75] Inventors: Tadashi Honkawa, Mito; Fujiya Takahata, Katsuta; Koichi Yagai, Mito; Yoshio Maeda; Tetuya Shinden, both of Katsuta, all of Japan

[73] Assignee: Hitachi, Ltd., Tokyo, Japan

[21] Appl. No.: 333,413

[22] Filed: Dec. 22, 1981

[30] Foreign Application Priority Data

Dec. 26, 1980 [JP] Japan .................. 55-183836

[51] Int. Cl.³ ........................... G01N 21/64
[52] U.S. Cl. .................. 250/461.2; 364/413
[58] Field of Search ........... 250/461.2; 364/413

[56] References Cited

U.S. PATENT DOCUMENTS 4,131,800 12/1978 Bruck et al. ............... 250/461.2

FOREIGN PATENT DOCUMENTS 55-109950 8/1980 Japan ..................... 250/461.2

Primary Examiner—Alfred E. Smith
Assistant Examiner—T. N. Grigsby
Attorney, Agent, or Firm—Antonelli, Terry & Wands

[57] ABSTRACT

Fluorescent dye is added to a sample including lymphatic cells stimulated by antic bodies to measure fluorescence polarization. The fluorescence polarization varies with time. The measurement is stopped after a predetermined measurement time, and the lymphatic cells are separated from the sample by filtering. In order to determine the fluorescence polarization in a filtering process, approximate equations of the reaction are determined based on the fluorescence polarization measured during the reaction process. Based on the approximate equations, the fluorescence polarization in the filtering process is calculated. The reaction process is approximated by both an approximate linear line and an approximate curve. A reaction data at a predetermined future time is calculated based on the two approximate functions so that a reliability of the resulting data is improved.

5 Claims, 13 Drawing Figures

FLUORESCENCE POLARIZATION ANALYZER

The present invention relates to a fluorescence polarization analyzer, and more particularly to a fluorescence polarization analyzer suitable for extrapolating a value of reaction at a predetermined time later from the results of measurements of change of reaction in time.

In a reaction process which changes in time, it may not be possible to directly obtain measurement data at a desired measurement time.

In one example, measurement data immediately before the stop of the reaction is to be obtained but a sample must be taken out of a measurement area in order to stop the reaction. In another example, two or more phenomena on one sample must be measured at the same instant. In other example, a certain component in reaction liquid is filtered although measurement data in the course of filtering is to be obtained. In those measurements, data at the desired measurement time is usually calculated by approximation based on the data measured at a limited duration of time.

In recent study on immunity of a subject or lymphatic cell per se, a great attention has been paid to blastformation of the lymphatic cell. The blastformation of the lymphatic cell is analyzed by adding fluorescent dye to the lymphatic cells stimulated by antigen antic body reaction or cell disintegration mitogen and measuring fluorescence polarization. When the lymphatic cell is blastformed, the activity of the lymphatic cell increases and fluidity increases under this condition, the fluorescence polarization reduces.

The fluorescence is generated by stimulating the lymphatic cell of human beings by photohemagglutinin (PHA) or cancer basic protein (Ca.BP) to give fluorescin diacetate. By analyzing the fluorescence polarization, a cancer lymphatic cell and a normal lymphatic cell can be disciminated. Accordingly, this analysis has been noticed in recent years. In this analysis, the fluorescence polarization must be measured by the extrapolation. It is carried out in the following manner. Liquid floating the stimulated lymphatic cells is irradiated by vertically polarized actinic light to measure vertical fluorescence quantity and horizontal fluorescence polarization quantity separately. Since it is not possible to measure both of them at a desired time, the extrapolation based on the measured data is used. In order to subtract the fluorescence quantity of the materials other than the lymphatic cells, the lymphatic cells are filtered and the fluorescence quantity of the filtered liquid is measured. The reaction stops when the lymphatic cells are filtered. The fluorescence polarization is to be analyzed at this moment, but it cannot be directly analyzed because the sample must be taken out of the measurement area. Accordingly, the measurement data at the time when the reaction stops must be determined by the extrapolation.

In the past, in order to trace the reaction, it has been widely used to read data from an analog output signal by linear approximation. Where the data at the desired time cannot be directly obtained, the data is usually obtained by drawing an extrapolation line on measured curve by a linear scale.

Such a method has low reading precision and includes a variance of data due to personal variance of operator. Accordingly, attempt has been made to digitally process the approximation based on the measured data. However, in the digital process approach, all data are read to carry out the approximation which, in many cases, tends to neglect the reaction process in the course of the calculation of the desired data.

When the fluorescence polarization analysis is used to detect cancer, a percentage of hit is an important factor. No serious problem might be raised when a normal patient is misjudged as a cancer patient because such an error can be corrected by close examination. On the other hand, it would be a serious problem if a cancer patient mere misjudged as normal. Accordingly, the percentage of hit must be high. The mere digital processing in the prior art is low in reliability.

It is an object of the present invention to provide a fluorescence polarization analyzer which assures a high reliability.

In accordance with the present invention, an approximate linear line and an approximate curve are drawn based on measurement data within a certain time period and a data at a predetermined time later is determined from these approximate lines.

Figure 1:
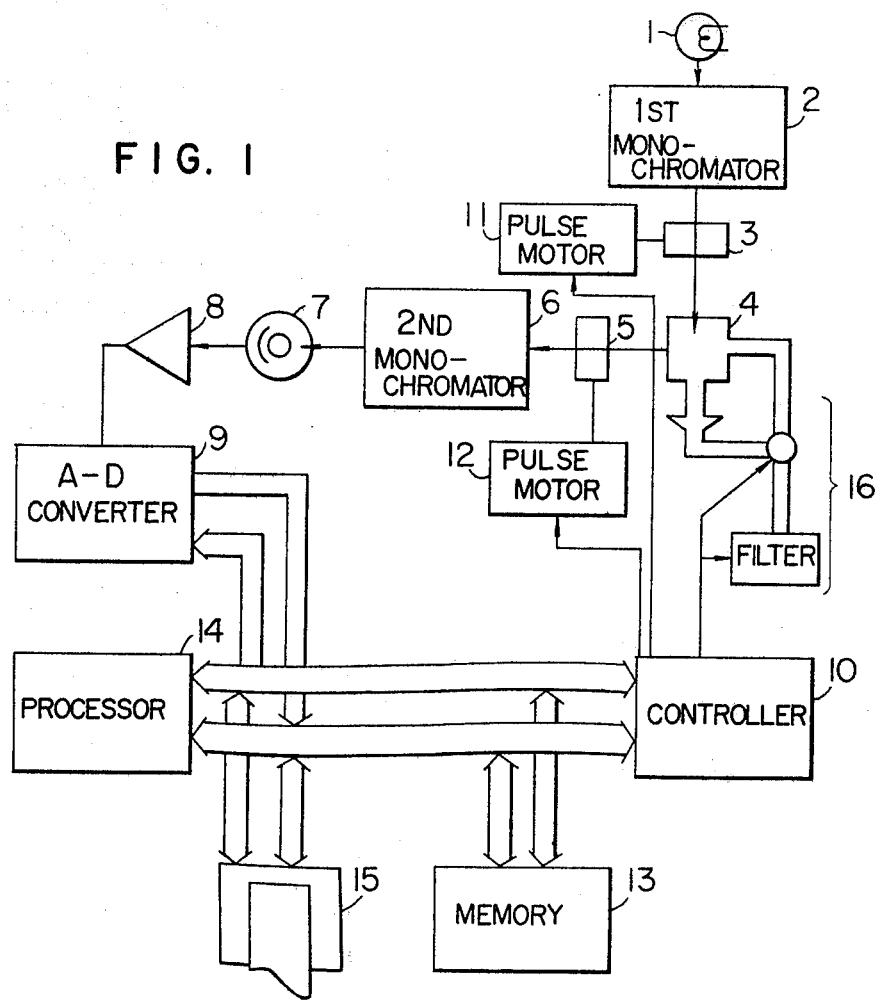
FIG. 1 shows a block diagram of one embodiment of the present invention.
Figure 2:
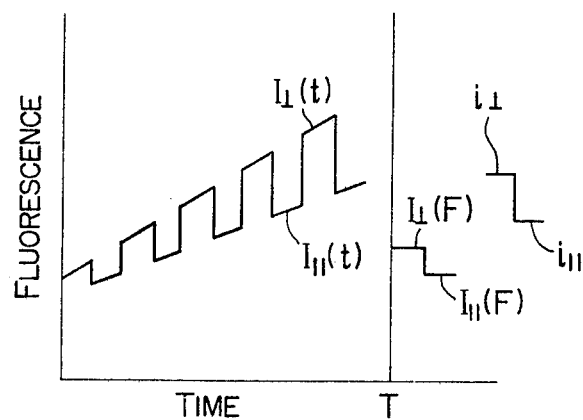
FIG. 2 shows a measurement data by one embodiment of the present invention.

Referring now to FIGS. 1 and 2, one embodiment of the present invention is explained.

A white light from a light source 1 is converted to a monochromatic light by a first monochromator 2. The monochromatic light is then polarized by a first polarizer 3 to irradiate a sample chamber 4. The sample, when it is irradiated, emits fluorescence. The fluorescence transmitted through a second polarizer 5 and a second monochromater 6 is converted to a monochromatic light. Only a light having a desired wavelength reaches a detector 7 which converts a light signal to an electric signal which is supplied to a pre-amplifier 8, thence to an A-D converter 9 where the signal is converted to a digital signal.

After the sample has been set in a sample chamber 4 and an operation switch has been turned on, a controller 10 issues an instruction to a pulse motor 11 so that the first polarizer 3 is set to pass only vertical component of the light. The controller 10 then issues an instruction to a pulse motor 12 to drive the second polarizer 5. The second polarizer 5 is repeatedly driven by 90 degrees at a constant time interval and the fluorescence emitted from the excited sample is divided into a component normal to the polarized exciting light and a component parallel thereto to produce reaction signals which vary with time as shown in FIG. 2. After A-D conversion, they are stored into a memory 13 as vertical components $I_\perp(t_1)$, $I_\perp(t_2)$, . . . and horizontal components $I_{//}(t_1)$, $I_{//}(t_2)$, . . . . After the measurement for a predetermined time period, the controller 10 instructs to an automatic filter unit 16 to filter the sample, and filtered liquid is again filled into the sample chamber 4. A time T from the start of measurement to an intermediate time of filtering is calculated and written into the memory 13.

The filtered liquid is measured in the same manner as that described above and the resulting signals $I_\perp(F)$ and $I//(F)$ are stored into the memory 13. In response to the instruction of the controller 10, the first polarizer 3 is rotated by 90 degrees (horizontally) and the measurement is carried out in the same manner as that described above, and the resulting signals $i_\perp$ and $i//$ are stored into the memory 13. The vertical components and the horizontal components of the written measurement data $I_\perp(t_1)$, $I//(t_1)$, $I_\perp(t_2)$, $I//(t_2)$, . . . are separately processed. In a processor 14, approximate linear functions $I_{1\perp}(t)$ and $I_{1//}(t)$ and approximate quadratic functions $I_{2\perp}(t)$ and $I_{2//}(t)$ are generated by minimum square method. The data measured at the end of reaction time T (intermediate time of filtering) are placed in those equations to produce data at the end of reaction time T, i.e. $I_{1\perp}(T)$, $I_{1//}(T)$, $I_{2\perp}(T)$ and $I_{2//}(T)$. The processor 14 further carries out the following operations:

$$G = i_\perp \div i_\|$$
$$I_{1\|} = I_{1\|}(T) - I\|(F)$$
$$I_{1\perp} = I_{1\perp}(T) - I_\perp(F)$$
$$I_{2\|} = I_{2\|}(T) - I\|(F)$$
$$I_{2\perp} = I_{2\perp}(T) - I_\perp(F)$$
$$P_1 = \frac{I_{1\|} - GI_{1\perp}}{I_{1\|} + GI_{1\perp}}, P_2 = \frac{I_{2\|} - GI_{2\perp}}{I_{2\|} + GI_{2\perp}}$$

In this manner, fluorescence dispolarization $P_1$ by the approximate linears functions and fluorescence dispolarization $P_2$ by the approximate quadratic functions are simultaneously obtained. The results are printed out on a graphic printer 15.

Figure 3:
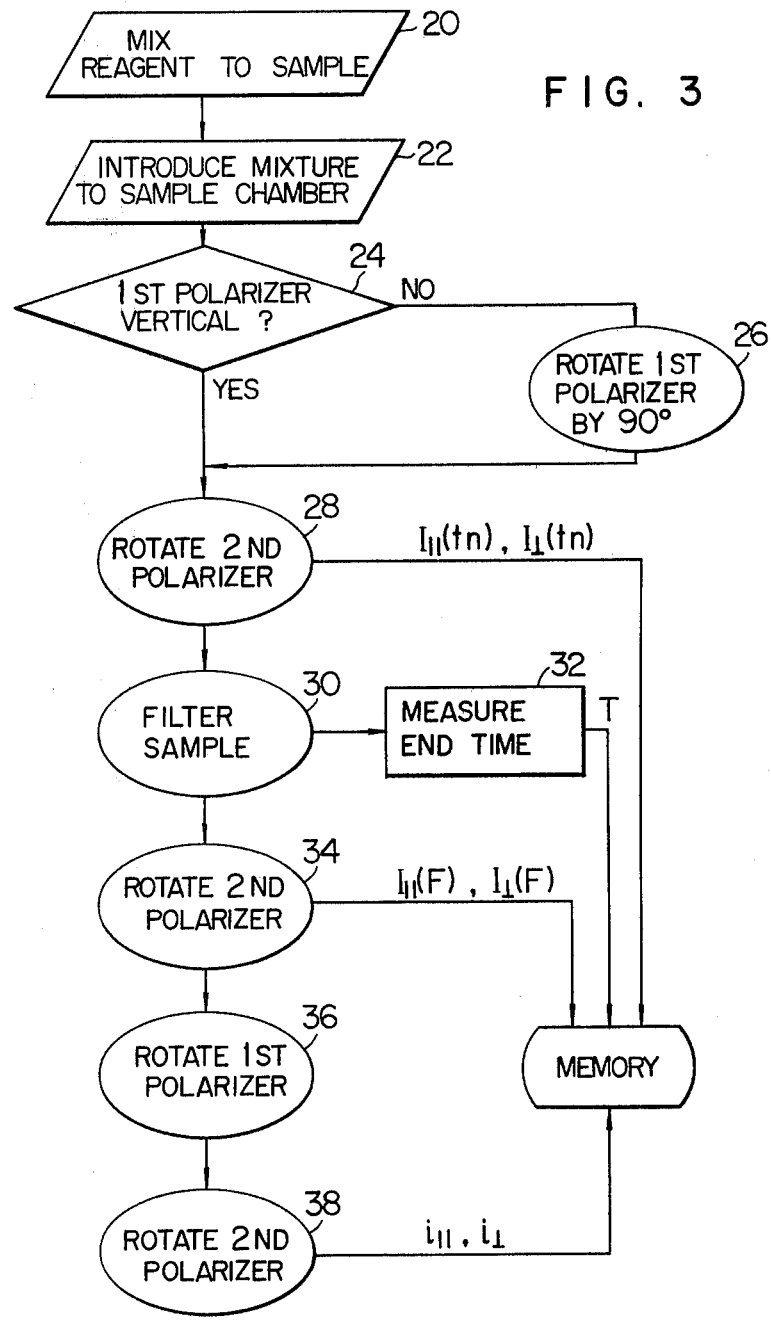
FIGS. 3 and 4 show flow charts of one embodiment of the present invention.
Figure 4:
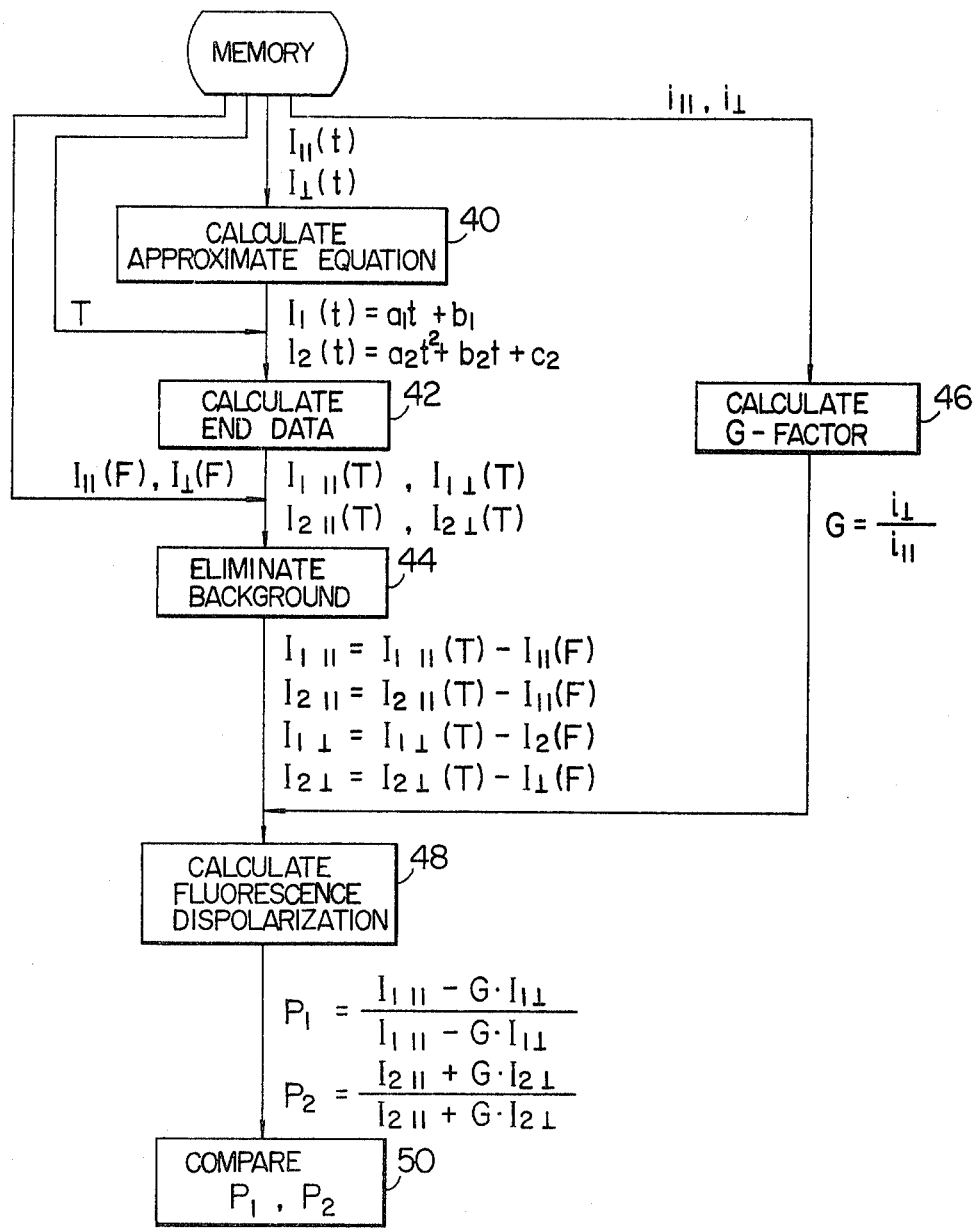

FIGS. 3 and 4 show flow charts for the above embodiment.

A regent is added to a lymphatic cell taken out of blood and they are mixed (step 20). The mixture is injected to the sample chamber 4 (step 22). A vertical component of the exciting light is extracted to excite the sample. In a decision step 24, the direction of the first polarizer 3 is checked. If it is horizontal, the first polarizer 3 is rotated by 90 degrees into vertical orientation (control step 26). As the measurement starts, the second polarizer 5 is repeatedly rotated by 90 degrees relative to the first polarizer 3 (control step 28) to repeatedly receive the normal component and the parallel component and the synchronized input signals $I//(t_1)$, $I_\perp(t_1)$, $I//(t_2)$, $I_\perp(t_2)$, ... $I//(tn)$, $I_\perp(tn)$ are read and stored in the memory 13. After the predetermined time period T, the sample is automatically filtered (control step 30). In a step 32, the end of reaction time T is calculated and stored in the memory 13, and the filtered liquid is returned to the sample chamber 4. In a control step 34, the measurement is again carried out and the measurement data $I//(F)$ and $I_\perp(F)$ which are synchronized with the rotation of th second polarizer 5 are stored in the memory 13 as floating background. In a control step 36, the first polarizer 3 is rotated by 90 degrees and the measurement is repeated. In a control step 38, the measurement data $i//$ and $i_\perp$ which are synchronized with the rotation of the second polarizer 5 are stored in the memory 13. After the measurement has been completed, the calculation starts in a calculation step 40 based on the data stored in the memory 13. The approximate linear function $I_1(t)=at+b$ and the approximate quadratic function $I_2(t)=at^2+bt+c$ are calculated by the minimum square method based on the measurement data $I//(t_1)$, $I//(t_2)$, $I//(t_3)$, . . . $I_\perp(t_1)$, $I_\perp(t_2)$, $I_\perp(t_3)$, . . . to produce $I_{1//}(t)$, $I_{1\perp}(t)$, $I_{2//}(t)$ and $I_{2\perp}(t)$. The end of reaction data $I_{1//}(T)$, $I_{1\perp}(T)$, $I_{2//}(T)$ and $I_{2\perp}(T)$ are obtained based on the stored end of reaction time T (step 42). By processing the stored background data $I//(F)$ and $I_\perp(F)$, background free reaction data $I_{1//}$, $I_{1\perp}$, $I_{2//}$ and $I_{2\perp}$ are obtained (step 44). An instrument factor G is calculated based on the stored data $i//$ and $i_\perp$ (step 46) and the fluorescence dispolarizations $P_1$ and $P_2$ are calculated based on the background free reaction data and the system factor G (step 48). The resulting fluorescence dispolarizations $P_1$ and $P_2$ are compared (step 50) to verify the reliability of the data.

Figure 5:
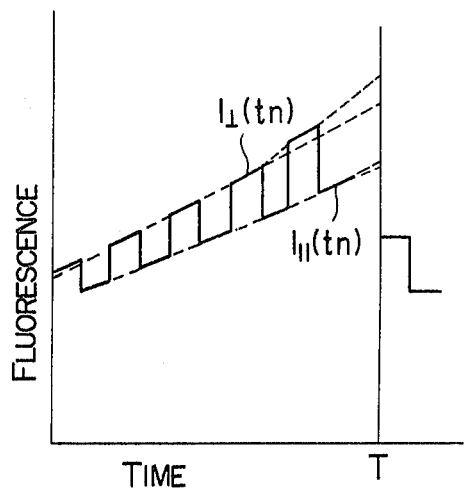
FIGS. 5 and 6 show other embodiments of the present invention.

FIG. 5 shows an exemplary measurement data for a normal reaction. The reaction is not linear but slightly bowed. The measurement data are shown below:

$I_{1//}=50.4$, $I_{1\perp}=61.0$
$I_{2//}=52.5$, $I_{2\perp}=62.3$
$I//(F)=21.1$, $I_\perp(F)=30.0$
$i//=42.0$, $i_\perp=28.6$
$G=0.682$ The fluorescense dispolarizations $P_1$ and $P_2$ are 0.162 and 0.175, respectively, which are different from each other.

Living body samples including the lymphatic cell are inherently suspensions or changed to suspensions by cohesion when they react with reagents. In the spectrophotometric measurement of those samples, the reactions are inherently non-linear or the reactions are apparently non-linear by the influence of scatter due to sedimentation of the suspension.

Figure 6:
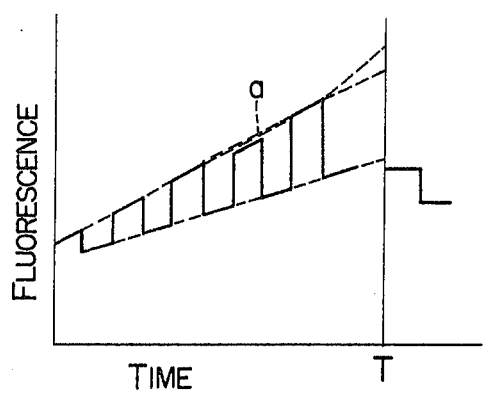

In the linear approximation, the response is relatively insensitive to the change in the output signal due to a fluctuation of the measurement signal by an external factor such as a fluctuation of the light source or a fluctuation of the measuring light due to a change in the sample such as cohesion, and a high reproducibility of data is attained, but a large measurement error is included for the non-linear reaction. Accordingly, for the non-linear reaction, the linear approximation is not effective and non-linear approximation is necessary. However, depending on a particular situation of the sample, for example, when the measurement data vary due to the cohesion (portion a in FIG. 6), the linear approximation is hardly affected by the variation but the non-linear approximation is highly affected by the variation resulting in the variation in the measurement data. An example of the measurement data is shown below:

$I_{1//}=57.8$, $I_{1\perp}=73.9$
$I_{2//}=57.5$, $I_{2\perp}=76.1$
$I//(F)=31.8$, $I_\perp(F)=45.0$
$G=0.682$ The fluorescence dispolarizations $P_1$ and $P_2$ are 0.138 and 0.096, respectively. It is thus seen that the approximate quadratic function materially deviates from the approximate linear function resulting in improper value of $P_2$. In the present invention, the shortcomings of the linear approximation and the nonlinear (quadratic) approximation are compensated for each other by simultaneously calculating $P_1$ and $P_2$. By comparing $P_1$ and $P_2$, the reliability of the measurement data is improved.

An example in which a change in an optical intensity of a product when the optical measurement of a reaction of living body related material is done, changes in muddiness and cohesion in reaction solution, sedimentation of particles and decomposition of reagent at an early stage of reaction are experimentarily analyzed and compared with an approximate equation derived from measured data for the change in order to eliminate a phenomenon resulting from uninherent reactions to reduce an error, is now explained.

FIGS. 7 to 10 show approximate functions derived from measured data.

Figure 7:
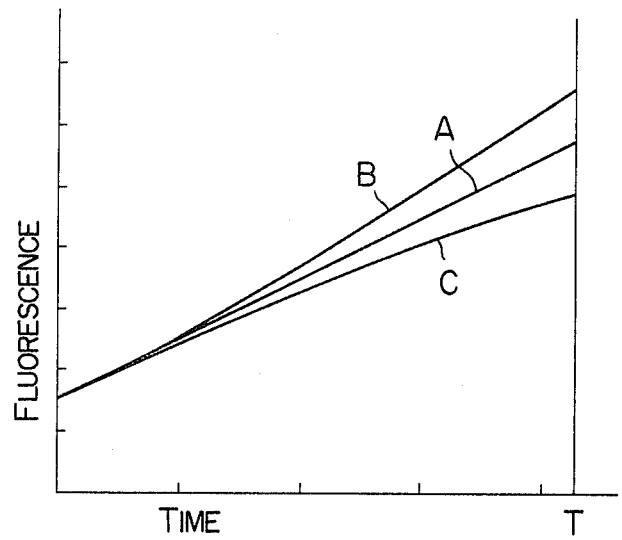
FIGS. 7 to 10 show further embodiments of the present invention.

An approximate linear function $I=10t+15$ shown by a line A in FIG. 7 illustrates a reaction which changes linearly with time. A curve B is approximated by a function $I=0.5t^2+10t+15$ and indicates that material in reaction solution is stimulated to accelerate the reaction. A curve C is approximated by a function $I=-0.5t^2+10t+15$ and indicates that the material in the reaction solution coheres or settles to impede the reaction.

For the curves B and C, a polarity of a coefficient of the time (t) is discriminated by the processor 14 to determine the status of the reaction. The decision made by the processor 14 is displayed on the display 15.

Figure 8:
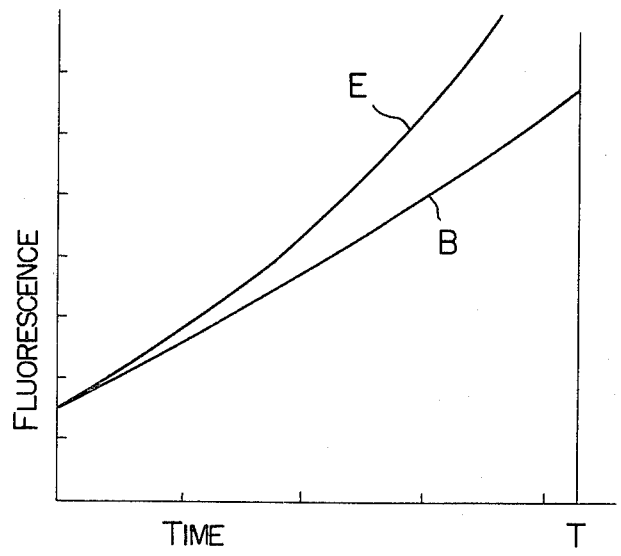

A curve B shown in FIG. 8 is represented by an approximate equation $I=0.5t^2+10t+15$ and a curve E is represented by an approximate equation $I=2t^2+10t+15$. The curve E shows that the reaction is unusually accelerated.

To compare the curves B and E, a coefficient of the square term of the time (t) for the curve E is four times as large as that for the curve B. Accordingly, by checking if the coefficient of the square term is within a predetermined range, the normality or abnormality of the reaction can be determined.

Figure 9:
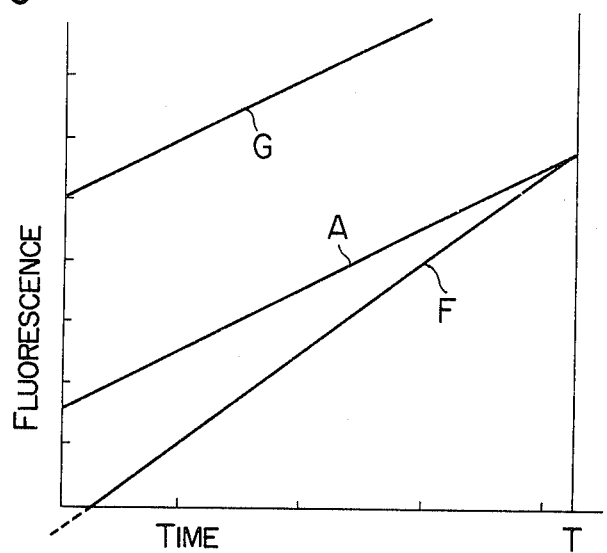

A line A shown in FIG. 9 is represented by $I=10t+15$ and a line F is represented by $I=14.75t-5$. The lines A and F assume the same value at a time $T_f$ but the line F has a negative value at the time $T=0$ (start of reaction) indicating abnormality in an initial reaction condition.

Accordingly, by checking if the value of the approximate equation at the time $T=0$ is positive or negative, the abnormality of the reaction can be determined.

A line G in FIG. 9 is represented by $I=10t+50$. To compare the line G with the line A, the value of the former at the start of reaction time is more than three times as large as the value of the latter indicating the abnormality by the decomposition of the reagent at the initial stage of the reaction. Accordingly, by checking if the value of the line at the time $T=0$ i.e., on the vertical axis is within a predetermined range, the abnormality due to the decomposition of the reagent can be determined.

Figure 10:
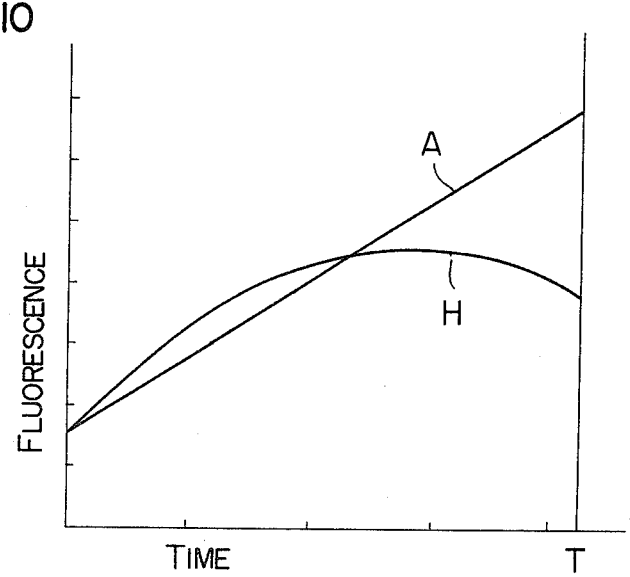

A curve H shown in FIG. 10 is represented by $I=-3.75t^2+21.25t+15$ and indicates that the cohesion and the sedimentation in the reaction solution are very high. For the present approximate equation, the coefficient of the square term of the time t is negative and 7.5 times as large as that of the curve C.

As illustrated above, by checking if the coefficient of the variable of the approximate equation and the value of the equation when the time $T=0$ are positive or negative, and if they are within predetermined ranges, the abnormality of the reaction can be detected and hence the reliability of the data can be improved.

The measurement of the reaction process in accordance with the present embodiment offers the following advantages.

(1) The occurrence of a phenomenon which impedes an inherent reaction can be checked and hence the reliability of the measurement data is improved.

(2) By outputting the check results described above, information including the status of the reaction, the presence or absence of sub-reaction, the presence or absence of the phenomenon which impedes the reaction and the decomposition or degradation of the reagent can be provided to an operator.

(3) By checking the coefficient of the approximate equation, a deviation from a desired reaction, for example, a linear reaction, can be quantitatively detected.

(4) When an approximate equation for a reaction process is to be generated to determine an unmeasured value at a desired time, it can be effectively determined without providing a separate determination mechanism.

Figure 11:
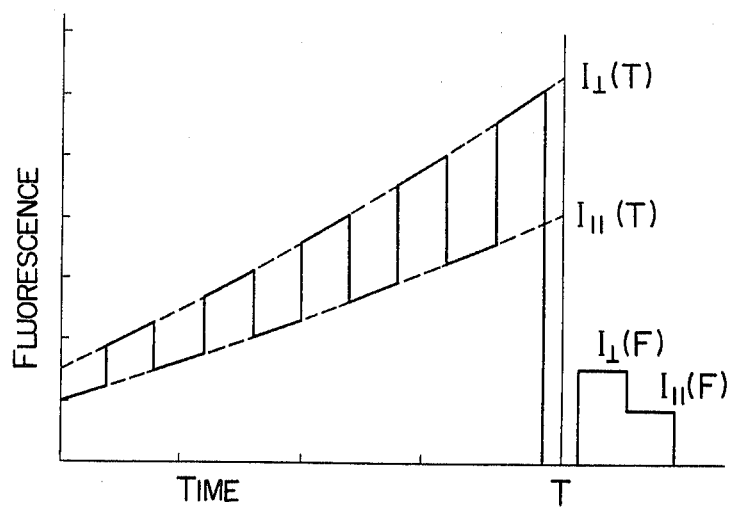
FIGS. 11 and 12 show still further embodiments of the present invention.
Figure 12:
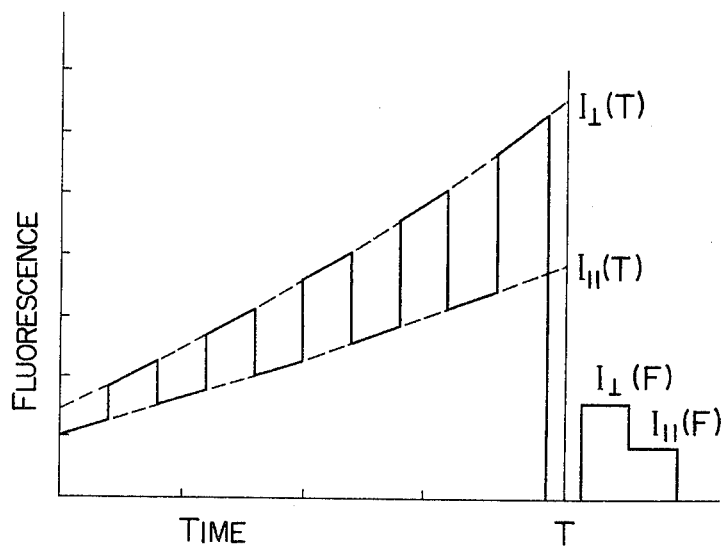

Examples of measurement in accordance with the present embodiment are shown in FIGS. 11 and 12. Solid lines show measured data and broken lines show approximate functions.

The reaction does not always proceed linearly but in many cases traces a curve. Accordingly, in the present invention, both the vertical component and the horizontal component are approximated by a linear function on by a non-linear (quadratic) function, or one of the components is approximated by the linear function and the other component is approximated by the quadratic function so that the approximation is carried out to reflect the measured data. As seen from FIG. 12, the horizontal component of the light signal fits the linear approximation while the vertical component of the light signal fits the quadratic approximation. They are observed as the measured data. For such measurement data, if both components are approximated by the linear functions or the quadratic functions, an error of the extrapolated value will increase.

The fluorescence polarization P derived from the aforementioned equation naturally includes an error if $I_\perp(T)$ and $I//(T)$ include errors. If the extrapolated value, $I_\perp(T)$ and $I//(T)$ are approximated to values far from the actual reaction, the value P will not also reflect the actual reaction.

In the present embodiment, the three resulting approximate values and the fluorescence polarization P are printed by the printer.

The present embodiment offers the following advantages:

1. An advantage of the conventional manual approximation (extrapolation by a linear scale) is utilized and an error in approximating a non-linear reaction by a linear function is reduced to improve a precision of the extrapolated value.

2. By using not only the extrapolative approximation by the linear approximation but also the approximation by the quadratic approximation or the combination of the linear approximation and the quadratic approximation, the approximation which more exactly reflects the actual reaction can be attained.

3. Troublesome manual approximation by an operator is avoided and a personal error of the operator is avoided.

4. Where one component changes linearly while the other component changes quadratically, the present embodiment is very effective.

5. By calculating the fluorescence polarization P based on the extrapolated values derived from the linear approximation, the quadratic approximation and the combination thereof, and displaying P, numeric information indicating the process of the reaction can be presented to the researcher.

When a solution including cells such as lymphatic cells and suspended particles such as insoluble protein is to be optically measured, the suspension itself and filtrate having particles filtered by a porous filter are measured.

However, it is difficult to determine an optimum condition of filtering. In the suction filtering of the living body related material, decomposition of particles may occur. In certain instances, the solution includes a high background which makes it difficult to detect a change in a reaction caused by the particles. When the solution includes unstable material, it may even self-decompose in a short time.

Figure 13:
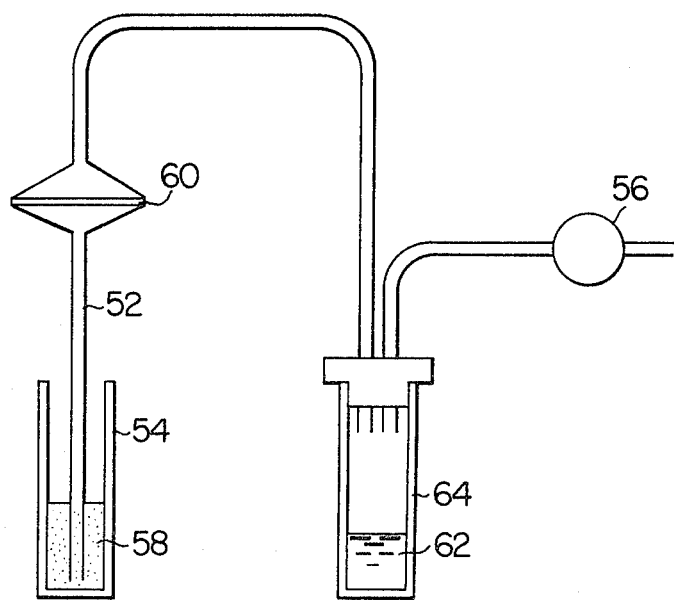
FIG. 13 shows a sample filtering unit in one embodiment of the present invention.

FIG. 13 shows a filtering system in accordance with the present embodiment. When the controller 10 issues a filtering instruction, a sampling tube 52 is moved into a sample measuring cuvette 54 by a vertically moving mechanism, not shown. A valve 56 connected to a suction pump, not shown, is then opened so that suspension 58 in the cuvette 54 is sucked and filtered by a porous filter 60. The suspended particles are eliminated by the filter 60 and filtrate 62 is recovered into a filtrate measuring cuvette 64. After the filtering, the filtrate measuring cuvette 64 is placed at a light measuring position and a fluorescence polarization of the filtrate is measured.

In FIG. 2, a vertical component value of the suspension at time t is shown by $I_\perp(t)$, and a horizontal component value is shown by $I//(t)$. A vertical component value of the filtrate is shown by $I_\perp(F)$ and a horizontal component value is shown by $I//(F)$.

If the fluorescence polarization of the particle free solution is higher than the fluorescence polarization of the suspension particles, $I_\perp(F)$ and $I//(F)$ rise. If the fluorescence components in the particles dissolve into the solution by the decomposition of the particles, $I_\perp(F)$ and $I//(F)$ also rise. Ratios (in percentage) of the fluorescence polarizations of the suspension to the fluorescence polarizations of the filtrate for the respective samples are shown below.

TABLE 1

| Sample Number | Ratio of Reaction Solution to Filtrate (in %) | |
|---|---|---|
| | $I_{f//}/I_{s//}$ | $I_{f\perp}/I_{s\perp}$ |
| 1 | 44.0% | 49.1% |
| 2 | 26.0 | 32.3 |
| 3 | 26.9 | 32.2 |
| 4 | 25.5 | 31.3 |
| 5 | 27.6 | 33.2 |
| 6 | 62.1 | 67.3 |
| 7 | 25.4 | 31.0 |
| 8 | 57.8 | 64.9 |
| 9 | 24.2 | 30.2 |
| 10 | 25.1 | 31.3 |
| 11 | 23.6 | 28.9 |
| 12 | 21.8 | 26.6 |
| 13 | 36.5 | 42.3 |
| 14 | 52.4 | 58.6 |
| 15 | 31.5 | 38.1 |
| 16 | 34.8 | 40.7 |
| 17 | 45.3 | 50.8 |
| 18 | 44.1 | 49.1 |
| 19 | 36.9 | 41.2 |
| 20 | 65.3 | 74.7 |

Table 1 shows measurement data for twenty samples. Samples No. 6 and No. 20 show high ratios $I//(F)/I//(T)\times 100$ and $I_\perp(F)/I//(T)\times 100$, which are higher than 60%. When 60% ratio is used as a reference, the samples No. 6 and No. 20 are determined to be abnormal.

From Table 1, it is apparent that a relation of $I//(F)/I//(T) < I_\perp(F)/I//(T)$ exists. It indicates that the vertical component reflects the changes in filtering and reaction in advance to the horizontal component.

For example, in the sample No. 8, the ratio for the vertical component is higher than 60% while the ratio for the horizontal component is lower than 60%. If 60% value is selected as a reference, the ratio for the vertical component exceeds the reference and abnormality is detected in a primary check. For the samples No. 6 and No. 20, since their vertical component ratio and horizontal component ratio both exceed 60%, abnormality is detected in both primary and secondary checks.

The processor 14 shown in the embodiment of FIG. 1 (which is usually a microcomputer) determines if the resulting ratio of the fluorescence polarizations is within a predetermined range. A display unit displays the calculation result and the determination result.

In the present embodiment, when the fluorescence intensity increases by the decomposition of the reagent or the effluence of the fluorescence component into the solution occurs by the decomposition of the particles, an alarm signal (primary check) is issued based on the vertical component which reflects the influence by the change in advance to the horizontal component, and an alarm signal (secondary check) indicating the abnormality of the measured data and low reliability of the data is issued based on the horizontal component.

In the present embodiment, a level of the background of the liquid relative to the suspension particles can be determined. As a result, the self-decomposition and the aging of the reagent can be detected. The decomposition of the particles during the reaction or the filtering and the effluence from the particles can also be detected. When the two-level check by the two components is done, the information such as abnormality or alarm can be presented to the operator in advance. Because of the two-level check, the check in processing the data is more perfect and the reliability of the data is improved.

What is claimed is:

1. A fluorescence polarization analyzer comprising:
   means for irradiating a polarized exciting light to a sample;
   means for detecting a component of a predetermined polarization direction of fluorescence emitted from said sample;
   first processing means for determining an approximate linear line based on data in a selected time period detected by said detection means and calculating a data at a predetermined future time based on said approximate line; and
   second processing means for determining an approximate curve based on said data in said selected time period detected by said detecting means and calculating a data at said predetermined future time based on said approximate curve.

2. A fluorescence polarization analyzer according to claim 1 further comprising means for comparing said data calculated by said first processing means with said data calculated by said second processing means.

3. A fluorescence polarization analyzer according to claim 1 further comprising means for checking a coefficient of a variable of an approximate equation representative of said approximate linear line determined by said first processing means and outputting a check result.

4. A fluorescence polarization analyzer according to claim 1 further comprising means for checking a co-efficient of a variable of an approximate equation representative of said approximate curve determined by said first processing means and outputting a check result.

5. A fluorescence polarization analyzer according to claim 1 wherein said detection means detects perpendicularly intersecting two polarization components, said first processing means processes the data of one of said two polarization components, said second processing means processes the data of the other polarization component, and further comprising means for calculating a fluorescence polarization based on the data calculated by said first and second processing means.

* * * * *